United States Patent [19]

Bühler et al.

[11] 4,165,967

[45] Aug. 28, 1979

[54] PROCESS FOR DYEING HUMAN HAIR WITH DIAZO SALTS AND COUPLING COMPONENTS

[75] Inventors: Arthur Bühler, Rheinfelden; Alfred Fasciati, Bottmingen; Walter Hungerbühler, Riehen, all of Switzerland

[73] Assignee: Henkel Kommanditgesellschaft auf Aktien, Düsseldorf-Holthausen, Fed. Rep. of Germany

[21] Appl. No.: 827,402

[22] Filed: Aug. 24, 1977

[30] Foreign Application Priority Data

Sep. 2, 1976 [CH] Switzerland .................. 11135/76

[51] Int. Cl.$^2$ ............................................. A61K 7/13
[52] U.S. Cl. ............................................. 8/10.1; 8/10; 8/41 R; 8/46; 8/47
[58] Field of Search .................. 8/10, 10.1, 41 R, 46, 8/47; 260/156

[56] References Cited

U.S. PATENT DOCUMENTS

| | | | |
|---|---|---|---|
| 3,231,471 | 1/1966 | Lange | 8/10.1 |
| 3,582,253 | 6/1971 | Berth et al. | 8/10.1 |
| 3,955,918 | 5/1976 | Lang | 8/10 |
| 4,025,301 | 5/1977 | Lang | 8/10.1 |
| 4,065,254 | 12/1977 | Buhler et al. | 8/47 X |

Primary Examiner—James O. Thomas, Jr.
Assistant Examiner—Vera C. Clarke
Attorney, Agent, or Firm—Hammond & Littell

[57] ABSTRACT

Described is a process for dyeing keratin-containing material with developing dyes by applying diazo salts and coupling components successively, in any desired sequence, to the material to be dyed, and coupling them with each other, characterized in that there are used as coupling components specific derivatives of hydroxypyridine or pyridone.

13 Claims, No Drawings

PROCESS FOR DYEING HUMAN HAIR WITH DIAZO SALTS AND COUPLING COMPONENTS

The present invention relates to a process for dyeing keratin-containing material with developing dyes formed from a diazo salt and a coupling component which contains a 6-membered nitrogen heterocycle.

There have hitherto been used for dyeing keratin-containing material, particularly human hairs, oxidation dyes, for example those based on phenylenediamine and benzidine. These dyes have various disadvantages, especially of a physiological nature. Attempts have therefore been made to find for keratin-containing material a dyeing process which overcomes these disadvantages.

It is known to dye keratin-containing material with developing dyes which are formed from a diazo salt and a coupling component, for example a benzene or naphthalene derivative or 1-phenyl-3-methylpyrazolone-5. These coupling components however react with the diazo salt relatively slowly and, furthermore, different coupling components are necessary to obtain all the shades desired.

A novel process for dyeing keratin-containing material with developing dyes has now been found, in which process diazo salts and coupling components containing a 6-membered nitrogen heterocycle are applied successively, in any desired sequence, to the material to be dyed, and coupled with each other.

This process is characterised in that there is used a coupling component of the formulae (1), (2) or (3)

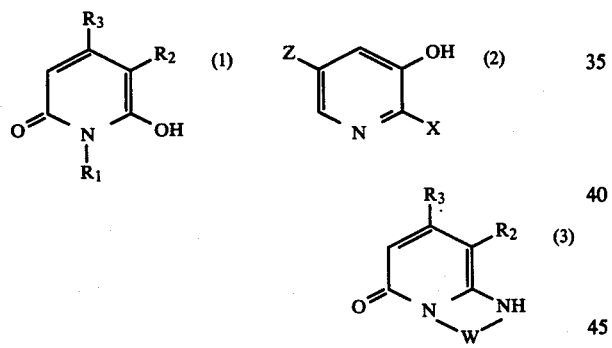

wherein
R₁ represents hydrogen or a monovalent organic radical, for example an aryl group such as phenyl or naphthyl, an alkyl or cycloalkyl group such as methyl, ethyl, propyl, isopropyl, butyl, hexyl, 2-ethylhexyl, octyl or cyclohexyl, with these groups being optionally substituted by cyano, a sulphonic acid group or carboxylic acid group, halogen such as fluorine, chlorine or bromine, hydroxyl, an alkoxy group such as methoxy, ethoxy, propyloxy, isopropyloxy or hydroxyethoxy, a quaternary ammonium group such as the trimethylammonium group, or by an acylamino group such as acetylamino, chloroacetylamino or benzoylamino, or an acylaminoalkyl group in which the acyl moiety is reactive, such as the mono- or dichlorotriazine group, the di- or trichloropyrimidine group, the difluoro- or difluorochloropyrimidine group, the vinyl sulphone, vinylsulphonamide, acrylamide or α-halogenoacrylamide group, or a phenylene, diphenylene or alkylene group which has at most 6 carbon atoms and which can be optionally substituted by chlorine, methyl or methoxy groups and which links the radical of the formula (1) with a further similar pyridone group by way of the nitrogen atom, or the direct bond with the nitrogen atom of a further similar pyridone group; preferably, $R_1$ represents hydrogen or a straight-chain or branched-chain alkyl group having 2 to 10 carbon atoms, or an alkyl group substituted by an OH, $SO_3H$, COOH, CN or $OCH_3$ group or by a reactive group;

$R_2$ represents cyano, aminocarbonyl or an alkyl group substituted by a water-solubilising carboxylic acid group or sulphonic acid group, such as sulphomethyl or sulphoethyl, particularly a cyano, aminocarbonyl or sulphomethyl group;

$R_3$ represents an alkyl group which has up to five carbon atoms and which is optionally substituted by a carboxylic acid group or sulphonic acid group, such as methyl or ethyl, or a phenyl group which can optionally carry in the p-position a further similar pyridone group, preferably an ethyl group and in particular a methyl group;

X represents the OH or $NH_2$ group;
Z represents a hydrogen or halogen atom, and
W represents a bridge member, especially an alkylene radical of the formula $-(CH_2)_2-$ or $-(CH_2)_3-$, or an o-phenylene group of the formula

The compounds of the formula (1) constitute particularly interesting coupling components.

Among these, the compounds which are particularly suitable in the process according to the invention are those wherein
$R_1$ represents hydrogen or a straight-chain or branched-chain alkyl group having 2 to 10 carbon atoms, or an alkyl group substituted by an OH, $SO_3H$, COOH, CN or $-OCH_3$ group or by a reactive group,
$R_2$ represents a cyano, aminocarbonyl or sulphomethyl group, and
$R_3$ represents the methyl or ethyl group.

The following compounds are of special importance:

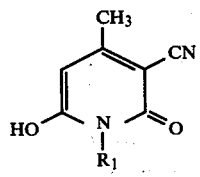

with $R_1$ = H, $C_2H_5$, $CH_2CH_2SO_3H$, $CH_2CH_2COOH$, $CH_2CH_2CN$, $CH_2CH_2OH$, $CH_2CH_2OCH_3$, 2-ethyl-hexyl, cyclohexyl, benzyl, or phenyl -continued

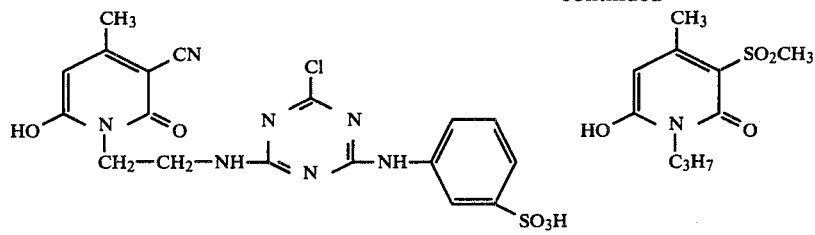

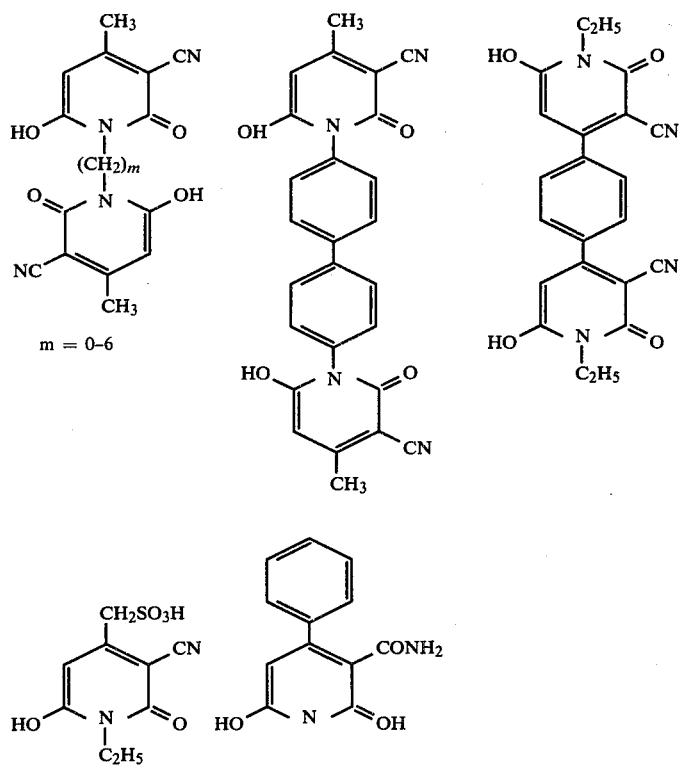

Of very special importance are the coupling components of the formulae:

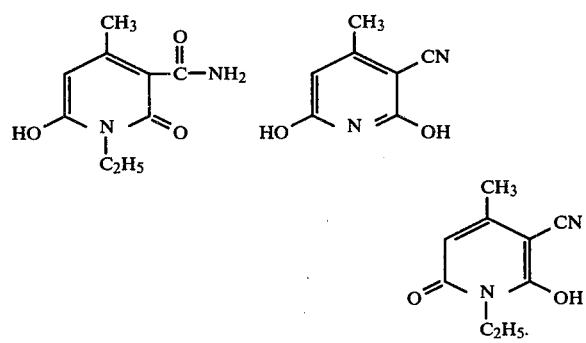

Coupling components of the formula (2) more especially suitable are those wherein X represents the $NH_2$ group and Z represents a hydrogen atom.

All these compounds can exist in several tautomeric forms.

In order to simplify the description, these compounds are represented in only one of these tautomeric forms. It is to be however expressly emphasised that the description, here and in the following, especially in the Claims, relates always to compounds in any one of these tautomeric forms.

These coupling components are for the most part known, or they can be obtained by known methods; for example as described in The Chemistry of Heterocyclic Compounds, Pyridine and its Derivatives, Parts I–IV, Interscience Publishers Inc., New York, Interscience Publishers Ltd., London; 1960–1964; also in 'Berichte der Deutschen Chemischen Gesellschaft' 29 (1896), page 655, as well as in numerous Patent Specifications, for example the British Pat. Nos. 1,256,094 and 1,256,095; the Dutch Pat. Specifications Nos. 71,06678 and 71,09361, the U.S. Pat. No. 3,471,506, the German Offenlegungsschriften Nos. 1,964,690, 2,022,817, 2,118,945, 2,123,061 and 2,141,449, and also the French Offenlegungsschriften Nos. 2,025,723 and 2,027,586.

As diazo components, which are necessary as the second component for the synthesis of the dye, it is possible to use the diazotised aromatic or heteroaromatic amines known from the chemistry of azo compounds, particularly monoamines, especially aminobenzenes and aminonaphthalines. In particular, also the commercial diazo components or salts thereof from the naphthol process are suitable for the process according to the invention.

The following may be mentioned as examples of amines which can be used after diazotisation: 2- or 3- chloroaniline hydrochloride, 2-, 3- or 4-nitroaniline, 2-methoxyaniline hydrochloride, 2,5-dichloroaniline, 3,5-di-trifluoromethylaniline, 2-chloro-5-trifluoromethylaniline, 2-methoxy-5-chloroaniline hydrochloride, 2-methyl-3-chloroaniline hydrochloride, 2-methyl-5-chloroaniline hydrochloride, 2-methyl-4-chloroaniline hydrochloride, 2-nitro-4-chloroaniline, 2-trifluoromethyl-4-chloroaniline, 2-nitro-4-methylaniline, 2-nitro-4-methoxyaniline, 2-nitro-4-ethoxyaniline, 2-methyl-4-nitroaniline or 2-methyl-5-nitroaniline, 2-methoxy-4-nitroaniline or 2-methoxy-5-nitroaniline, 2-ethylsulphonyl-5-trifluoromethylaniline, 3-ethylsulphonyl-6-methoxyaniline, 3-N,N-diethylaminosulphonyl-6-methoxyaniline, 3-N-n-butylaminosulphonyl-6-methoxyaniline, 1,4-diamino-2,6-dichlorobenzene, 2,4-dimethyl-3-nitroaniline, 2-methoxy-4-methyl-5-nitroaniline, 2-chloro-4-cyano-5-methylaniline, 2,5-dimethoxy-4-cyanoaniline hydrochloride, 4-phenylaminoaniline, 2-methoxy-4-phenylaminoaniline, 4-(4'-methoxyphenylamino)-aniline hydrosulphate, 4',4''-diaminodiphenylaminehydrosulphate, 2-phenylsulphonylaniline, 2-(4'-chlorophenoxycarbonyl)-aniline, 3-benzylsulphonyl-6-methoxyaniline, 2,5-diethoxy-4-(2'-methylphenoxyacetylamino)-aniline, 2,5-dimethoxy-4-(4'-methyl-phenoxyacetylamino)-aniline, 2,5-diethoxy-4-(4'-methyl-phenoxyacetylamino)-aniline, 2-phenoxy-5-chloroaniline, 2-(4'-chlorophenoxy)-5-chloroaniline or 2-(4'-chlorophenoxy)-5-chloroaniline hydrochloride, 4-aminoazobenzene, 4-aminoazobenzene hydrochloride, 3-methoxy-4-aminoazobenzene, 2',3-or 2,3'-dimethyl-4-aminoazobenzene hydrochloride, 2,5-dimethoxy-4'-nitro-4-aminoazobenzene, 2-methyl-5-methoxy-4,4'-diaminoazobenzene, 2-ethyl-5-methoxy-4-amino-4'-chloroazobenzene, 2-methyl-5-methoxy-4-amino-2'-nitro-4'-methylazobenzene, 2-amino-4-methoxy-5-methyl-2'-chloro-4'-nitroazobenzene, 2,5-dimethoxy-4-amino-2'-N,N-dimethylaminocarbonyl-4'-nitroazobenzene, 2,5-dimethoxy-4-amino-2',6'-dichloro-4'-nitroazobenzene, 2-chloro-4-benzoylamino-5-methoxyaniline, 2,4-dimethyl-5-benzoylaminoaniline, 2-N,N-diethylaminosulphonyl-4-benzoylamino-5-methoxyaniline, 2-methoxy-4-benzoylamino-5-methylaniline, 2,5-dimethoxy-4-benzoylaminoaniline, 2,5-diethoxy-4-benzoylaminoaniline, 3,3'-dimethylbenzidine, 3,3'-dimethoxybenzidine, 4-(1'-naphthylazo)-aniline, 1-(2'-ethoxyphenylazo)-4-aminonaphthalene, 2-methyl-4-amino-5-ethoxy-4'-(4''-aminophenylamino)-azobenzene, 1- or 2-aminonaphthalene, 3-benzoylamino-4-methoxyaniline hydrochloride and 1-aminoanthraquinone.

These amines firstly have to be diazotised. This can be performed by customary methods, for example by means of sodium nitrite and mineral acid, e.g. hydrochloric acid. Free amines are converted before diazotisation into their salts, if necessary by heating with moderately concentrated acid, which is diluted before diazotisation. Instead of using diazotised amines, it is also possible to use dye salts, i.e. stabilised diazonium compounds. Suitable stabilisers and separating reagents for the dye salts are: metal chlorides such as $ZnCl_2$, $CdCl_2$, $CoCl_2$ or $MnCl_2$, which can be separated with the diazo compound as a complex from the aqueous solution, aromatic sulphonic acids which can be used as free acids or also as alkali salts, and which form with diazonium compounds true salts, particularly naphthalenedisulphonic acids, hydrofluoboric acid, which likewise forms with diazo compounds true salts, and acylaminoaryl-sulphonic acids, such as acetylsulphanilic acid. In some cases, also the diazonium chlorides or acid sulphates themselves can be separated and used. The stabilized diazonium salts contain also inert salts. With the use of dye salts, an addition of alkali-binding agents, such as acetic acid, formic acid, sodium acetate/acetic acid, chromium acetate or mono- or disodium phosphate, is in some cases necessary if coupling is performed in an alkaline solution, since dye salts are broken down by alkali action. The addition of a dispersing agent is advantageous. The keratin-containing material impregnated with the coupling component as defined is not sensitive to air, so that an addition of stabilisers or the like to the solution containing the coupling component is not necessary.

As an aftertreatment of the dyeing, a soaping of the dyed material with soap or with a synthetic detergent or dispersing agent and sodium carbonate and a water softener can be performed. This aftertreatment gives better fastness to rubbing and purer shades.

The actual dyeing process comprises two stages, namely the application of one of the two components of the developing dye and the subsequent "development," that is to say, the coupling with the second component. Preferably, the coupling component is firstly applied and then the diazo component. At the same time, the process conditions are governed by the nature of the keratin-containing material to be dyed. If this is living material, e.g. the hairs of a person or of an animal, the coupling and diazo components are applied at a pH value which is compatible with the skin, preferably between 5 and 8, and at about 15° to 40° C., preferably at body temperature, for example by spraying, or by applying in the form of a solution, creme, emulsion or gel. The reaction time in the case of the component first applied is about 1 to 20, preferably 2 to 10, minutes. The material is then optionally rinsed and the second component is applied, preferably in the same manner as the first. The time required for the coupling reaction is about 0.5 to 20, preferably 1 to 10, minutes. The dyed hair is subsequently rinsed, optionally with the addition of surface-active agents, and finally dried.

Dead material, such as skins, furs, feathers or wigs from human hair, are impregnated with solutions of the coupling or diazo components, in a pH range of about 2 to 12, preferably 4 to 10 and particularly 5 to 8, preferably by immersion in these solutions. The temperature for this can be for example up to 60° C. After impregnation with the first component, the keratin-containing material can be optionally squeezed out or centrifuged before it is impregnated with the second component necessary for the formation of the dye.

The solution of the coupling component is preferably obtained by introducing the coupling component into water and then adding alkali, e.g. ammonia, until a clear solution results. The diazo components, which are preferably used as stabilised diazonium salts, are employed in the form of acid or neutral aqueous solutions.

Coupling and diazo components are preferably used in approximately equal molar amounts. An excess of up to about 100% of one component is however usually not harmful.

In the process according to the invention, the coupling and diazo components can be used as homogeneous substances. Since however in the dyeing of keratin-containing material mixed shades are frequently desired, mixtures of the coupling components and/or in particular of the diazo components are preferably used.

The concentration of the solutions is generally between 0.1 and 10%, preferably between 0.5 and 5%, of coupling and diazo components, respectively, relative to the total weight.

For producing cremes, emulsions or gels, the solution of the coupling and diazo components, respectively, are provided with the customary additives, such as wetting agents and detergents, preferably nonionic additives, such as the addition products of ethylene oxide with fatty acids, fatty alcohols or fatty amines, and also anion-active additives, such as alkylsulphonates, alkylbenzenesulphonates or fatty alcohol sulphonates.

The solutions, cremes, emulsions or gels can moreover contain further additives, for example thickeners such as starch or methylcellulose, Vaseline, paraffin oils, perfumes, or finishing agents such as pantothenic acid or cholesterol. These additives are employed in the usual amounts.

The process according to the invention is suitable in particular for shading or dyeing grey or bleached keratin-containing material; it can however be applied also for the cross-dyeing of dyed keratin-containing material.

There are obtained by this process dyeings which have good fastness properties in service, such as good fastness to light, to washing and to rubbing, and which in many cases also display a beautiful lustre.

Compared with the known dyeing processes with developing dyes, in which other coupling components are used, the process according to the invention is distinguished by a number of advantages: the impregnation with the coupling component can be performed in many cases in the neutral or weakly acid range, in consequence of which the damage which occurs in the case of the alkaline pH values necessary for the customary coupling components is avoided; in addition, the coupling reaction occurs in a shorter space of time, a factor which offers advantages especially with regard to the industrial dyeing of furs and feathers; furthermore, it is possible with the process according to the invention to produce with only one coupling component, with variation of the diazo component, all shades of colour from light-yellow to black, whereas to achieve this with the known dyeing processes with developing dyes several coupling components are necessary.

The following Examples serve to further illustrate the invention. Percentages are percent by weight; parts are parts by weight and the temperatures are given in degrees Centigrade. The diazo components (amines) used were employed as stabilised diazo salts in commercial form. In the case of mixtures of diazo or coupling components, the value 1:1 denotes that equal parts by weight of the two constituents were used.

EXAMPLE 1

There is prepared a 1% aqueous solution of the coupling component of the formula

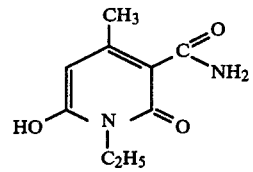

by introducing this into distilled water, and dissolving it by the addition of ammonia.

A bundle of grey human hairs weighing 0.3 g is immersed in 50 ml of the above solution, and is left in this solution for 15 minutes at room temperature.

The bundle of hair is subsequently removed from the solution; it is squeezed out briefly with a glass rod, and is then immersed in a 1% aqueous solution of the diazo salt of the amine of the formula

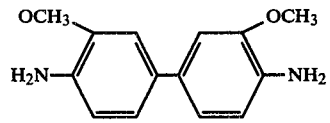

The hair is left for 5 minutes at room temperature in this solution; it is subsequently rinsed under running water and dried in air.

Hairs which are dyed violet-red and which have good fastness properties in service are obtained.

EXAMPLE 2

If the procedure is carried out exactly as described in Example 1 except that there are used, instead of the coupling and diazo components given in Example 1, the coupling and diazo components listed in the following Table, dyed hairs in the shades of colour shown in column 4 are obtained.

| Ex. | Coupling component | Diazo component | Colour on the hair |
|---|---|---|---|
| 2 | coupling component from Example 1 | ![] NH₂, 5 Cl (2-chloroaniline) | yellow |
| 3 | " | NH₂, OCH₃, H₃C, NHCO-phenyl | light-reddish brown |
| 4 | " | NH₂, Cl, Cl (dichloroaniline) | yellow |

-continued

| Ex. | Coupling component | Diazo component | Colour on the hair |
|---|---|---|---|
| 5 | " | 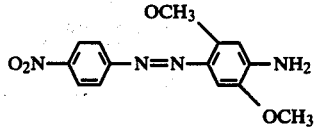 $O_2N-\text{C}_6H_4-N=N-\text{C}_6H_2(OCH_3)_2-NH_2$ | brown |
| 6 | " | 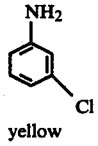 3-chloroaniline ($NH_2$, Cl) | yellow |
| 7 | 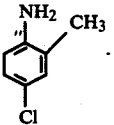 $NH_2$, $CH_3$, Cl | | yellow |
| 8 | " | 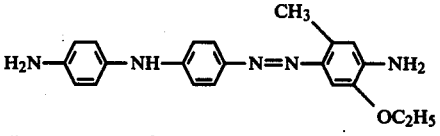 $H_2N-\text{C}_6H_4-NH-\text{C}_6H_4-N=N-\text{C}_6H_2(CH_3)(OC_2H_5)-NH_2$ | grey to black |
| 9 | 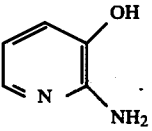 pyridine with OH, $NH_2$ | diazo component from Example 1 | violet-blue |
| 10 | " | diazo component from Example 2 | pink |
| 11 | " | diazo component from Example 3 | violet |
| 12 | " | diazo component from Example 4 | light-brown |
| 13 | 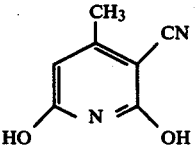 pyridine with $CH_3$, CN, HO, OH | diazo component from Example 3 | light-brown-reddish |
| 14 | " | diazo component from Example 4 | light yellow |
| 15 | coupling component from Example 1 + coupling component from Example 13 (1:1) | diazo component from Example 1 | violet |
| 16 | " | diazo component from Example 3 | reddish brown |
| 17 | " | diazo component from Example 4 | light yellow |
| 18 | " | diazo component from Example 1 + diazo component from Example 3 (1:1) | violet |
| 19 | " | diazo component from Example 1 + diazo component from Example 4 (1:1) | yellowish-brown |
| 20 | " | diazo component from Example 3 + diazo component from Example 4 (1:1) | reddish-yellow |

-continued

| Ex. | Coupling component | Diazo component | Colour on the hair |
|---|---|---|---|
| 21 | (structure: N-ethyl pyridinone with CH₃, CN, OH substituents) | diazo component from Example 1 + diazo component from Example 3 (1:1) | violet |
| 22 | " | diazo component from Example 1 + diazo component from Example 4 (1:1) | yellowish-brown |
| 23 | " | diazo component from Example 3 + diazo component from Example 4 (1:1) | yellow |
| 24 | coupling component from Example 13 | diazo component from Example 1 + diazo component from Example 3 (1:1) | violet |
| 25 | " | diazo component from Example 1 + diazo compoment from Example 4 (1:1) | yellowish-brown |
| 26 | " | diazo component from Example 3 + diazo component from Example 4 (1:1) | yellow |
| 27 | coupling component from Example 1 | 2-nitroaniline | olive yellow |
| 28 | " | 4-chloro-2-methylaniline | honey-yellow |
| 29 | coupling component from Example 9 | 4-aminodiphenylamine | reddish-brown |
| 30 | " | 2,5-diethoxy-4-benzoylamino-aniline | blue-violet |
| 31 | " | 2,5-dimethoxy-4-benzoylamino-aniline | dark violet |
| 32 | " | 4-methoxy-4'-amino-diphenylamine | dark brown |
| 33 | " | 2-methoxy-4-amino-diphenylamine | olive |
| 34 | coupling component from Example 21 | diazo component from Example 2 | olive yellow |
| 35 | " | diazo component from Example 4 | olive yellow |

-continued

| Ex. | Coupling component | Diazo component | Colour on the hair |
|---|---|---|---|
| 36 | " | 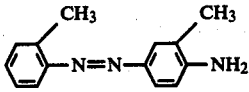 | English red |
| 37 | " | diazo component from Example 6 | olive brown |
| 38 | " | diazo component from Example 27 | olive brown |
| 39 | " | 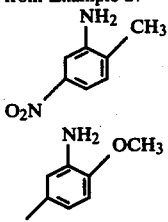 | olive brown |
| 40 | " |  | copper red |
| 41 | " | diazo component from Example 29 | violet-brown |
| 42 | " | diazo component from Example 30 | violet-brown |
| 43 | " | diazo component from Example 1 | violet-brown |
| 44 | " | diazo component from Example 31 | violet brown |
| 45 | " | diazo component from Example 32 | violet-black |
| 46 | 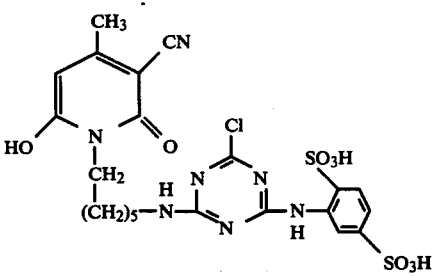 | 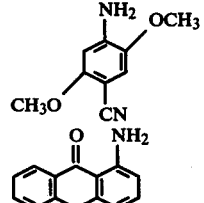 | reddish-gold |
| 47 | " | diazo component from Example 27 | olive yellow |
| 48 | " | 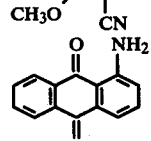 | autumn gold |
| 49 | " | 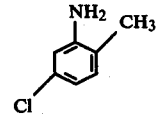 | autumn gold |
| 50 | " | 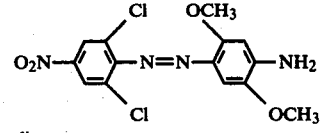 | olive brown |
| 51 | " | | reddish-brown |
| 52 | " | diazo component from Example 32 | dark brown |

EXAMPLE 53

If the procedure is carried out exactly as described in Example 1 except that to the solution of the coupling component or to that of the diazo salt is added, before introduction of the hairs, 1%, relative to the weight of the solution, of Turkey red oil or 5% of sodium lauryl sulphate, there are obtained in both cases dyeings dyed approximately twice as intensely as those according to Example 1.

EXAMPLE 54

10 g of a chrome tanned sheepskin, shorn to about 15 mm, is wetted back for one hour, in a dyeing drum, at 40° in 200 ml of an aqueous solution containing 0.2 g of anhydrous sodium carbonate, 0.2 g of ammonia (24%) and 0.1% of a nonionic detergent; the material is subsequently rinsed and centrifuged.

This material is introduced into 200 ml of a liquor at 25°, obtained by dissolving 0.1 g of the coupling component from Example 21 and 0.05 g of sodium carbonate with the subsequent addition of 0.1 ml of 85% formic acid, and is treated for 30 minutes in a dyeing drum at this temperature. The material is afterwards rinsed and centrifuged.

The sheepskin is then immersed in 200 ml of a liquor at 25°, which contains 0.4 g of the diazo component from Example 3 and 0.1 g of a nonionic detergent, and is treated for 30 minutes at 25°; it is subsequently rinsed, centrifuged and dried. The result is a sheepskin dyed red.

EXAMPLE 55

A creme emulsion is prepared by introducing 1 part of the coupling component from Example 1 into 75 parts of water, dissolving the coupling component by the addition of ammonia, and then adding 10 parts of fatty alcohol sulphate (sodium salt chain length $C_{12}$–$C_{18}$) and 10 parts of fatty alcohol (chain length $C_{12}$–$C_{18}$), and making up the quantity to 100 parts.

This emulsion is applied at room temperature to grey human hair by rubbing the emulsion into the hair, and allowing it to act for 15 minutes. The hair is afterwards briefly rinsed and, by rubbing-in, there is applied an emulsion obtained by stirring 1 part of the diazo salt from Example 1 and 10 parts of the above-employed fatty alcohol and fatty alcohol sulphate, respectively, into 79 parts of water. The emulsion is allowed to act for 5 minutes; the hair is then thoroughly rinsed with the addition of a customary detergent to thus obtain hair dyed violet-red.

We claim:

1. A process for dyeing human hair with developing dyes which comprises applying to said hair, at temperatures from about 15° C. to 40° C., an effective amount of aqueous solutions of diazo salts and coupling components successively, in any desired sequence, and coupling said diazo salts and coupling components with each other, wherein the coupling component is of the formula (1) or (2)

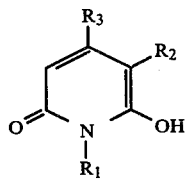 (1) 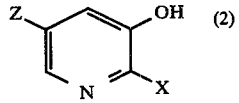 (2)

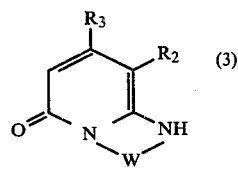 (3)

wherein
$R_1$ is hydrogen or a monovalent organic radical,
$R_2$ is cyano, aminocarbonyl or an alkyl group substituted by a carboxylic acid group or sulphonic acid group,
$R_3$ is an alkyl group which has up to five carbon atoms and which is optionally substituted by a carboxylic acid group or sulphonic acid group, or a phenyl group which can optionally carry in the p-position a further similar pyridone group,
X is the OH or $NH_2$ group, and
Z is a hydrogen or halogen atom, and the concentration of said solutions is between 0.1 and 10% by weight of said diazo salts and coupling components and said diazo salts and coupling components are present in the molar range of about 2:1 to 1:2.

2. The process of claim 1, wherein the coupling component is of the formula (1).

3. The process of claim 1, wherein the coupling component is of the formula (1) wherein $R_1$ is hydrogen or a straight-chain or branched-chain alkyl group having 2 to 10 carbon atoms, or an alkyl group substituted by an OH, $SO_3H$, COOH, CN or —$OCH_3$ group or by an acylamino group or an acylaminoalkyl group in which the acyl moiety is reactive; and $R_2$ and $R_3$ are as defined in claim 1.

4. The process of claim 1, wherein the coupling component is of the formula (1) wherein $R_2$ is a cyano, aminocarbonyl or sulphomethyl group; and $R_1$ and $R_3$ are as defined in claim 1.

5. The process of claim 1, wherein the coupling component is of the formula (1) wherein $R_3$ is a methyl or ethyl group; and $R_1$ and $R_2$ are as defined in claim 1.

6. The process of claim 1, wherein the coupling component is of the formula (1) wherein $R_1$ is hydrogen or a straight-chain or branched-chain alkyl group having 2 to 10 carbon atoms, or an alkyl group substituted by an OH, $SO_3H$, COOH, CN or —$OCH_3$ group or by an acylamino group or an acylaminoalkyl group in which the acyl moiety is reactive; $R_2$ is a cyano, aminocarbonyl or sulphomethyl group; and $R_3$ is the methyl or ethyl group.

7. The process of claim 1, wherein the coupling component is selected from those of the formulae

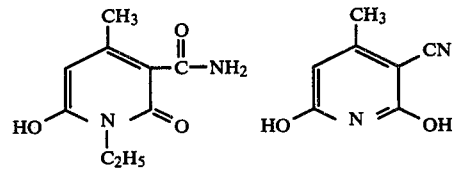

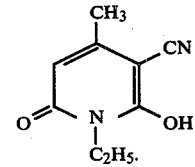

8. The process of claim 1, wherein the coupling component is of the formula 2 wherein X is the $NH_2$ group, and Z is a hydrogen atom.

9. The process of claim 1, wherein the diazo salts are stabilized diazonium compounds of monoamines.

10. The process of claim 9, wherein the diazo salts are stabilized diazonium compounds of aminobenzenes or aminonaphthalenes.

11. The process of claim 1, wherein the coupling component is a mixture of two or more of the coupling components.

12. The process of claim 1, wherein the diazo salts are a mixture of two or more diazo components.

13. The process of claim 1, wherein there is firstly applied to said hair at least one of the coupling components of the formula (1) or (2) and subsequently the diazo salt.

* * * * *

UNITED STATES PATENT AND TRADEMARK OFFICE
CERTIFICATE OF CORRECTION

PATENT NO. : 4,165,967

DATED : August 28, 1979

INVENTOR(S) : Arthur Bühler et al.

It is certified that error appears in the above-identified patent and that said Letters Patent are hereby corrected as shown below:

Column 4, line 57, "Offenlegungsschriften" should read

-- Patent Applications --.

Column 8, lines 29 - 33, the upper left-hand substituent "OCH$_3$"

should read -- H$_3$CO --;

Example 2 of the Table, the diazo component

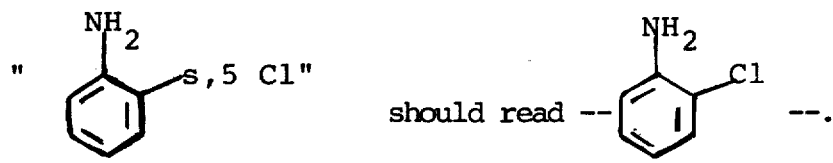

Columns 9 and 10, in the Table, Example 5, the diazo component should read:

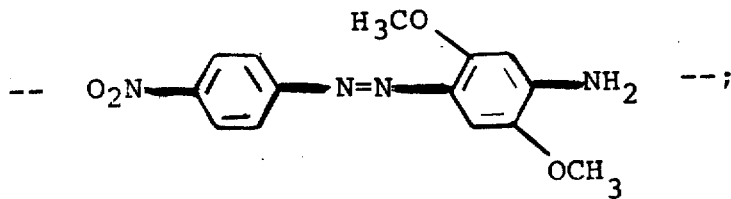

UNITED STATES PATENT AND TRADEMARK OFFICE
CERTIFICATE OF CORRECTION

PATENT NO. : 4,165,967
DATED : August 28, 1979
INVENTOR(S) : Authur Buhler et al.

It is certified that error appears in the above-identified patent and that said Letters Patent are hereby corrected as shown below:

Columns 9 and 10, in the Table, Example 7 should read:

— 7.   "   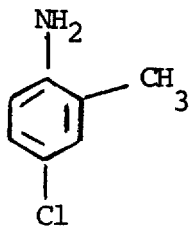   yellow —;

Example 16 should read:

— 16.   "   diazo component from Example 3   reddish brown —.

UNITED STATES PATENT AND TRADEMARK OFFICE
CERTIFICATE OF CORRECTION

PATENT NO. : 4,165,967

DATED : August 28, 1979

INVENTOR(S) : Arthur Buhler et al.

It is certified that error appears in the above-identified patent and that said Letters Patent are hereby corrected as shown below:

Columns 11 and 12, in the Table at Example 21, the coupling component should read:

-- 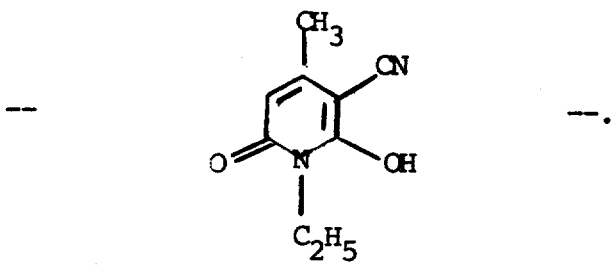 --.

Signed and Sealed this

Twenty-fifth Day of March 1980

[SEAL]

Attest:

Attesting Officer

SIDNEY A. DIAMOND

Commissioner of Patents and Trademarks